United States Patent [19]

Rosenthal et al.

[11] 3,962,302

[45] *June 8, 1976

[54] PRODUCTION OF ISOCYANATES FROM ESTERS OF CARBAMIC ACIDS (URETHANES)

[75] Inventors: Rudolph Rosenthal, Broomall; John G. Zajacek, Devon, both of Pa.

[73] Assignee: Atlantic Richfield Company, Los Angeles, Calif.

[ * ] Notice: The portion of the term of this patent subsequent to Nov. 11, 1992, has been disclaimed.

[22] Filed: July 18, 1975

[21] Appl. No.: 597,106

Related U.S. Application Data

[63] Continuation of Ser. No. 449,291, March 8, 1974, abandoned, which is a continuation-in-part of Ser. No. 357,301, May 4, 1973, abandoned.

[52] U.S. Cl............................................... 260/453 P
[51] Int. Cl.²....................................... C07C 118/00

[58] Field of Search................................. 260/453 P

[56] References Cited
UNITED STATES PATENTS
3,345,394  10/1967  Pelster et al........................ 260/453

FOREIGN PATENTS OR APPLICATIONS
48-1653  1/1973  Japan

*Primary Examiner*—Lewis Gotts
*Assistant Examiner*—Dolph H. Torrence
*Attorney, Agent, or Firm*—Delbert E. McCaslin

[57] ABSTRACT

Method for the production of isocyanates from esters of carbamic acids, (urethanes) by thermally decomposing the ester of the carbamic acid while said ester is dissolved in a suitable inert solvent to produce the isocyanate and alcohol and separately recovering the isocyanate and alcohol.

16 Claims, No Drawings

PRODUCTION OF ISOCYANATES FROM ESTERS OF CARBAMIC ACIDS (URETHANES)

CROSS REFERENCE TO RELATED APPLICATIONS

This is a continuation, of application Ser. No. 449,291 filed Mar. 8, 1974 now abandoned, which in turn is a continuation-in-part of Ser. No. 357,301 filed May 4, 1973, now abandoned.

BACKGROUND OF THE INVENTION

The conversion of esters of carbamic acids to the corresponding isocyanate and alcohol has been extensively investigated. An early Pat. U.S. No. 2,409,712 (1946) shows the pyrolysis of N-substituted carbamic esters in the liquid phase at subatmospheric pressures to give the isocyanate and alcohol. Thus ethoxyethoxyethyl N-lauryl carbamate was pyrolyzed in the liquid phase at 210° C. to 230° C. under high vacuum, i.e. 2 mm. Hg pressure, (no time given) to give lauryl isocyanate and ethoxyethoxyethanol. The yield of isocyanate was 75 percent. The use of such a high vacuum, however, poses problems in commercializing such a process and consequently it is not believed to have been commercialized. Other examples showed much lower yields down to 37 percent.

In an article in the Journal of the American Chemical society, Vol. 80, page 5495 et. seq. (1958), Dyer et al report that monomeric carbamates of the type RNHCOOR' are known to be degraded above 200° C. to the isocyanate and alcohol. The authors show, however, that biscarbamates prepared from methylenebis-(4-phenyl isocyanate) and 1-butanol, 2,2-dimethyl-1-propanol and benzyl alcohol and the polycarbamate from methylene-bis(4-phenyl isocyante) and 1,6-hexane diol when pyrolyzed at 300° C. produced carbon dioxide and the parent alcohol or diol and also yielded amine residues from the benzyl carbamate and polycarbamate.

In another article in the Journal of the American Chemical Society, Vol. 81, page 2138 et. seq. (1959) Dyer et al show that ethyl carbanilate gave phenyl isocyanate (60–75 mole percent based on carbanilate degraded, 44–30 percent degraded, in 6 hours and 4 hours, respectively) and the alcohol when heated at 200° C. under pressure sufficiently low 60–120 mm. Hg to vaporize the alcohol but high enough to retain the isocyanate. Thus even under these conditions other products were formed. At atmospheric pressure no phenylisocyanate was obtained, although 70 percent of the ethyl carbanilate was destroyed. At 250° C. and atmospheric pressure alpha-methylbenzyl carbanilate gave major amounts of aniline, alpha-methylbenzyl aniline, styrene and carbon dioxide.

Dicarbamates such as bis (2-acetoxyethyl) 1,6-hexane dicarbamate according to U.S. Pat. No. 3,054,819 (1962) can be distilled in the presence of a basic catalyst such as tribenzylamine at low pressures, for example, 6 mm. Hg at 215° C. to 260° C. to produce the hexamethylene diisocyanate at a yield of 40 percent. Without the catalyst a yield of only 17 percent was obtained.

A more recent British Pat. No. 1,247,451 (1971) discloses that it was known that organic isocyanates can be produced by the non-catalytic pyrolysis of urethanes at temperatures above 250° C. but the yield is undesirably low, and if lower temperatures are employed the isocyanate and alcohol will react to reform the original urethane. This confirms the findings discussed hereinbefore wherein various expedients such as catalysts and low pressures were employed with specific carbamates. The aforementioned British patent proposes to pyrolyze diethyl toluene-2,4-dicarbamate in the presence of a Lewis acid such as ferric chloride catalyst to produce toluene-2,4-diisocyanate (TDI). A yield of approximately 59 mole percent is shown. In general, the reaction is carried out at from 400° C. to 600° C. in the presence of the catalyst at subatmospheric pressures to form vapors, and condensing the vapors to recover the organic isocyanate product.

Thus although the monocarbamates can be noncatalytically pyrolyzed to the monoisocyanate and alcohol employing high temperatures and low pressures the yields are undesirably low. Likewise certain dicarbamates have been pyrolyzed to the diisocyanate and alcohol but the yields have generally been unsatisfactory for commercial purposes, moreover, in most cases the decomposition products are predominantly amines and carbon dioxide, not the desired diisocyanate. The aforementioned British patent also requires high temperatures and low pressures and in addition a Lewis acid catalyst such as ferric chloride which renders such process highly undesirable from a commercial viewpoint because of the highly corrosive nature of such acids.

The present invention obviates these problems and others encountered by the above illustrated prior processes. It can be carried out at atmospheric, subatmospheric or superatmospheric pressures. The present invention also does not require the use of catalysts and gives extremely high yields of the isocyanate and alcohol. It can be used with esters of carbamic acids in general, but is particularly useful for the production of the mono- and diisocyanates from their corresponding esters of mono- and dicarbamic acids.

SUMMARY OF THE INVENTION

This invention relates to a method for producing isocyanates from carbamates by thermally treating the carbamate in an inert organic solvent for the carbamate. Although esters of carbamic acids or carbamates are generically referred to as "urethanes" in the literature, the esters are usually individually named as a particular carbamate. The decomposition reaction produces the corresponding isocyanate and alcohol. If the alcohol is lower boiling it can be removed by the use of reduced pressure, by refluxing to distill it overhead or by employing an inert gas to sweep it from the reaction mixture. Conversely, if the alcohol is higher boiling than the isocyanate, the isocyanate can be separated overhead. Alternatively, both the alcohol and isocyanate can be vaporized and separated for example, by fractionation in the vapor phase.

It is an object of this invention, therefore, to provide a method to generate isocyanates from esters of carbamic acid.

It is another object of this invention to convert the esters of carbamic acids to isocyanates without the use of catalysts or low pressures.

It is another object of this invention to thermally decompose esters of carbamic acids in an inert solvent to produce high yields of the isocyanate.

It is another object of this invention to convert esters of dicarbamic acids in an inert solvent to produce the corresponding diisocyanate.

Other objects of this invention will be apparent from the description of the invention which follows and from the claims.

DESCRIPTION OF THE INVENTION

In accordance with this invention an isocyanate is produced from an ester of a carbamic acid. Representative carbamate starting materials may be characterized by the formulas $R(NHCOOR')_x$ or $(RNHCOO)_xR'$ wherein R is a substituted or unsubstituted mono-, di- or trivalent organic radical selected from saturated or monoolefinic unsaturated straight or branched chain aliphatic or cycloaliphatic radicals containing not more than 32 carbon atoms, alkoxyalkyl radicals having not more than 32 carbons with one or more ether linkages, aryl radicals, aralkyl radicals, and alkaryl radicals containing 1 to 5 rings which may be either condensed or non-condensed; R' is a substituted or unsubstituted mono-, di- or trivalent organic radical, preferably mono- or divalent, selected from saturated or monoolefinic unsaturated, straight or branched chain aliphatic or cycloaliphatic radicals containing not more than 32 carbon atoms, and preferably not more than 18 carbon atoms, similar alkoxyalkyl radicals, aryl radicals, aralkyl radicals and alkaryl radicals containing 1, 2 or 3 rings either condensed or non-condensed; and x is 1, 2 or 3, each R or R' being the same or different, respectively, when x is 2 or 3.

Preferably R will be an organic aliphatic radical containing up to 18 carbon atoms for example, methyl, ethyl, propyl, isopropyl, butyl, isobutyl, amyl, isoamyl, neopentyl, the hexyls, the heptyls, the octyls, the nonyls, the decyls, and the like including the octadecyl, and the monoolefinic compounds such as propenyl, butenyl, pentenyl, hexenyl, decenyl and the like including octadecenyl radials. The divalent radicals such as ethylene, propylene, butylene, amylene, hexylene, heptylene, octylene, nonylene, decylene and the like up to octadecylene also are included and likewise the trivalent radicals. These radicals may be hydrocarbyl or may be substituted with groups non-reactive with isocyanates, for example, nitro or halo, in particular chloro groups. Also included are the cycloaliphatic radicals containing from 5 to 7 carbon atoms preferably such as the cyclopentyl, cyclohexyl and cycloheptyl radicals, likewise the di- and trivalent corresponding radicals. The mono-unsaturated $C_5$ to $C_7$ cycloaliphatic radicals are also included as well as the substituted compounds wherein the substituent is a lower alkyl radical of 1 to 4 carbon atoms, or nitro, or halo such as chloro. The alkoxyalkyl radicals can range from the short chain such as methoxymethyl and ethoxyethyl to the longer chain radicals such as ethoxyethoxyethyl, propoxypropyl, butoxybutyl and the like up to 18 carbon atoms.

Likewise R can be an aryl radical such as the mono-, di- and trivalent radicals of benzene, toluene, naphthalene, diphenyl, anthracene, phenanthrene, terphenyl, naphthacene, and pentacene with the mono- and divalent radicals being particularly preferred. These aryl radicals can also be substituted with one or more lower alkyl groups preferably having from 1 to 4 carbon atoms or by radicals non-reactive with isocyanates such as nitro or halo, particularly chloro radicals. In addition to the alkaryl radicals, the aralkyl radicals, such as methyl, ethyl, propyl, and butyl radicals having a hydrogen substituted by phenyl, naphthyl, anthryl or phenanthryl radicals thus the lowest member of the group is methyl having a phenyl radical substituted for a hydrogen on the methyl giving a benzyl radical. Likewise more than one hydrogen may be substituted with a phenyl group as in diphenyl methane, the corresponding aralkyl radical being diphenylmethyl.

Preferably the R' of the above formula will be an organic radical containing up to 18 carbon atoms, i.e. the same alkyl radicals enumerated above for R, the same monoolefinic compounds enumerated for R the same alkoxyalkyl radicals enumerated for R and the same aryl radicals up to 3 rings enumerated for R.

Representative esters of carbamic acids as characterized above include ethyl phenylcarbamate (alternatively named ethyl N-phenylcarbamate or also the ethyl ester of carbanilic acid, or preferably ethyl carbanilate), butyl carbanilate, pentyl carbanilate, hexyl carbanilate, octyl carbanilate, ethylene dicarbanilate, 1,3-propylene dicarbanilate, 1,4-butylene dicarbanilate, 1,5-amylene dicarbanilate, 1,6 hexylene dicarbanilate, 1,8-octylene dicarbanilate, 1,10-decylene dicarbanilate, glyceryl tricarbanilate, ethyl 1-naphthalenecarbamate, ethyl 1-anthracenecarbamate, ethyl 2 ethyl 9-anthracenecarbamate, diethyl 9,10-anthracenedicarbamate, diethyl 1,5-anthracenedicarbamate, diethyl 5,6-naphthacenedicarbamate, diethyl 6,13-pentacenedicarbamate, ethyl para-phenylcarbanilate, ethylene bis(paraphenylcarbanilate), diethyl metabenzenedicarbamate, diethyl 1,5-naphthalenedicarbamate, methyl isopropylcarbamate, ethyl (methoxymethyl) carbamate, methyl sec-butylcarbamate, ethyl(3-chloropropyl)carbamate, methyl tertiary butylcarbamate, ethyl tert-octylcarbamate, diethyl tetramethylenedicarbamate, ethyl 1-ethyl-cyclohexanecarbamate, propyl (5,5-dimethylhexyl) carbamate, methyl para-toluenecarbamate, ethyl para-(trifluoromethyl) carbanilate, isopropyl meta-chlorocarbanilate, ethyl 2-methyl-5-nitrocarbanilate, ethyl 4-methyl-3-nitrocarbanilate, diethyl 4,4-methylenedicarbanilate, dimethyl meta-benzenedicarbamate, dimethyl toluene-2,4-dicarbamate, diethyl toluene-2,4-dicarbamate, dipropyl toluene-2,4-dicarbamate, diisopropyl toluene-2,4-dicarbamate, dibutyl toluene-2,4-dicarbamate, diamyl toluene-2,4-dicarbamate, dihexyl toluene-2,4-dicarbamate, diphenyl toluene-2,4-dicarbamate, di(phenylmethyl) toluene-2,4-dicarbamate, dinaphthyl toluene-2,4-dicarbamate, di(ethoxyethyl)toluene-2,4-Dicarbamate, the corresponding esters of toluene-2,6-dicarbamate, diethyl 4-chloro-meta-benzenedicarbamate, methyl para-butoxy carbanilate, ethyl para-acetylcarbanilate, ethyl para-bromocarbanilate, ethyl ortho-nitrocarbanilate, isopropyl meta-(trifluoromethyl)carbanilate, triethyl 1,3,5-benzenetricarbamate and the like. These esters specifically named are obviously merely representative of the very large number of esters falling within the definition of the general formula for the compounds which can be converted to isocyanates by the method of this invention. In general, the methyl and ethyl esters are more readily available and therefore these are more preferred.

In carrying out the process of this invention the ester is added to a solvent, to be characterized completely hereinafter in an amount such that substantially all of the ester will be completely dissolved at the reaction temperature. The ester can either be added to the cold solvent and the mixture heated to reaction temperature, which method is generally employed in smaller scale batch runs, or the ester can be added to the heated solvent continuously as would be more feasible for commercial large scale operations.

The process can be carried out at temperatures ranging from 175° C. to 350° C. with a more preferred range being from 200° C. to 300° C.

The reaction time can vary from several minutes to several hours depending upon the particular ester of the carbamic acid being reacted and the reaction temperature employed. In general times ranging from 5 minutes to 4–6 hours are sufficient to obtain the desired objectives of this invention in batch runs, while in continuous runs, residence times of from 100 to 20 hours are preferred.

The process is preferably carried out at atmospheric pressure when suitable high boiling solvents are employed, or it can be run at superatmospheric pressures when lower boiling solvents are used. Subatmospheric pressures can also be used with high boiling solvents but these subatmospheric pressures are not required for the reasons as set forth in the prior art wherein no solvents were used.

It is important in carrying out the process of this invention that the ester of the carbamic acid be substantially completely dissolved in the solvent at reaction temperature during conversion to the isocyanate and alcohol. If the alcohol is lower boiling than the isocyanate as most frequently is the case, then the alcohol can either be distilled from the solvent as formed or by being removed by the assistance of an inert gas being passed through the solution such as through a fritted disc or similar means for dispersion or by the use of a lower boiling solvent meeting the same criteria as will be set forth hereinafter and boiling between the isocyanate and alcohol. By this means recombination of the alcohol and isocyanate is prevented. Moreover, since the reaction is carried out in solution the formation of polymerization products such as tars and resins is avoided as well as inhibiting the formation of undesirable byproducts such as amines and carbon dioxide formerly associated with the thermal decomposition of esters of carbamic acids.

Alternatively if the alcohol is higher boiling than the generated isocyanate, the isocyanate can be removed overhead again by distillation or by the use of an inert gas or by the use of a suitable solvent also to be defined.

In a somewhat more sophisticated alternative which is preferred for continuous operation both the alcohol and isocyanate after formation in the solution are removed into the vapor phase either by the use of an inert gas or a suitable solvent. The isocyanate and alcohol are then separated by suitable fractionation and/or partial condensation. When a solvent is employed to carry the products overhead, it can be used to assist in the condensation of either the isocyanate or alcohol.

The inert gases which can be employed include nitrogen, helium, argon carbon dioxide, methane, ethane, propane and the like either alone or in mixtures. Nitrogen is preferred because of its convenience.

The solvents which can be used in the process of this invention both in the reaction medium and for carrying the products overhead are compounds which meet certain criteria. The reaction medium solvent must be capable of dissolving the particular ester of the carbamic acid at reaction temperature to an extent sufficient to make the process practical. Thus if the ester were soluble in the reaction medium solvent to the extent of 1 weight percent or less the process would be operable, but not particularly attractive from a commercial standpoint. Consequently, although the lower ester concentration limit might be considered to be about 1 weight percent, it is preferred that the ester be soluble at least to from 3 to 5 weight percent at reaction temperatures.

Since it is necessary in accordance with the objects of this invention to carry out the conversion of the ester of the carbamic acid in solution it is preferred that the concentration of the ester in the reaction medium solvent should not exceed from 70–80 weight percent based on the weight of the solution.

Both the reaction medium solvent and the solvent employed to carry the reaction product or products overhead (the carrier solvent) must not decompose at the reaction temperature employed and in addition these solvents cannot contain active hydrogens which, of course, would react with the isocyanate produced. In general any compound containing reactive groups that combine with the isocyanate should not be employed as these solvents in this invention.

Therefore, the parameters for suitable solvents in this invention are (a) compounds that are solvents for the starting carbamate (b) compounds that are stable at the reaction temperature and (c) compounds that are non-reactive with the generated isocyanate.

In view of these criteria or parameters, the compounds which can be used as reaction medium solvents in this invention include aliphatic, cycloaliphatic or aromatic hydrocarbons or substituted hydrocarbons or mixtures thereof, and also certain oxygenated compounds such as ethers, ketones, and esters. Other oxygenated compounds such as alcohols and acids cannot be used because of their reactivity with the generated isocyanate. Water also must, of course, be excluded. The sulfur analogues of the ethers, ketones, and esters also can be employed. When operating at atmospheric pressure the boiling point of the solvent or solvent mixture should be at or above the desired operating temperature. Lower boiling solvents or mixtures of solvents can be used by employing superatmospheric pressures, however, since the reaction must be carried out in the liquid phase, the single solvent or solvent mixture cannot have a critical temperature below 175° C. (the minimum reaction temperature).

In general, the compounds preferred are the aromatic hydrocarbons having from 1 to 3 rings including the alkyl benzenes having from 1 to 15 carbon atoms in the alkyl group, the halo (particularly chloro) substituted and the mono-nitro substituted aromatics; the aliphatic hydrocarbons having 4 to 32 carbon atoms, the substituted aliphatics such as the halo (particularly chloro and fluoro) and mono-nitro substituted $C_4$ to $C_{32}$ aliphatics, the cycloaliphatic hydrocarbons and lower alkyl substituted cycloaliphatic hydrocarbons, the oxygenated compounds selected from the group consisting of ethers, ketones and esters having from 4 to 32 carbon atoms and the sulfur analogues of these compounds.

Thus more specifically suitable compounds either for the reaction medium or carrier solvent include alkanes or monoalkenes having from 5 to as many as 32 carbon atoms which can be either straight or branched chain such as the pentanes, hexanes, heptanes, octanes, nonanes, decanes and on up to the higher alkanes such as n-hexadecane, n-octadecane, eicosane, squalane and the like and the corresponding monoalkenes. Lower molecular weight compounds such as the $C_4$'s although having critical temperatures below 175° C. can be employed in conjunction with the compounds having critical temperatures above 175° C. provided that the mixture has a critical temperature above 175° C. The aromatics such as benzene, toluene, ortho-xylene, meta-xylene, para-xylene, mixtures of two or more of the xylenes, ethylbenzene, cumene, diisopropylbenzenes, dibutylbenzenes, naphthalene, lower alkyl substituted naphthalenes, substituted benzenes and substituted naphthalenes non-reactive with isocyanates such as the nitro or halogenated compounds for example, the chlorobenzenes, nitrobenzene, chloronaphthalenes and the like, diphenyl and substituted diphenyls, diphenyl methane, terphenyls, such as ortho-terphenyl, substituted terphenyls, anthracenes, phenanthrenes and the like can be employed with equal utility. Likewise cycloaliphatic hydrocarbons such as cyclopentane methyl cyclopentane, 1',1-dimethyl cyclopentane, ethyl cyclopentane, cyclohexane, methyl cyclohexane, ethyl cyclohexane, cycloheptane and others of 5 to 7 carbon atoms.

Ethers (including cyclic ethers) and polyether solvents which do not contain a substituent group which would react with an isocyanate can also be used, likewise other oxygen containing compounds such as the ketones, for example methyl ethyl ketone, esters, for example dibutyl phthalate, dihexyl phthalate, dioctyl phthalate, didecyl phthalate and the like are suitable as are the sulfur analogues of these compounds.

In summary compounds meeting the criteria which have been set forth can be employed as the reaction medium solvent or carrier solvent since in order to meet the objectives of the invention, the conversion of the ester of the carbamic acid to give the isocyanate and alcohol must take place in solution from which the isocyanate and alcohol can be recovered without reaction of the isocyanate with the solvent.

The following Examples are provided to illustrate the invention in further detail but these are not to be construed as limiting.

In the runs which follow except where noted differently the ester of the carbamic acid and solvent (when used) was placed in a pot containing a glass covered magnetic stirrer, a thermometer a nitrogen inlet extending below the liquid level and a 6 inch Vigreaux column was used. The overhead take off tube was connected to a trap maintained at room temperature and then to a set of two Dry-Ice traps to collect the alcohol. The column and overhead tube were not heated during these runs except where noted. In certain runs samples of the pot materials were taken with a syringe inserted through a septum during reaction and were immediately diluted with a weighed amount of dried tetrahydrofuran to insure solubility of the products. In other runs the entire reaction product was analyzed. The samples or entire product were analyzed by gas-liquid phase chromatography for the isocyanate and for the mono- and/or dicarbamate by analytical liquid chromatography. In the representative runs which follow the rate of nitrogen flow is generally about 10 liters per hour or higher. The nitrogen flow rate was merely adjusted to remove the alcohol as formed in the particular laboratory set up employed in these runs and was merely a matter of convenience, whereas in the alternative methods which would be used commercially employing solvents an inert gas would not be required.

EXAMPLE I

A mixture of 10 g ethyl carbanilate (0.0606 mols) and 50 g n-hexadecane was heated for 1 hour at 200° C. and for 2 additional hours at 220° C. in a nitrogen stream at 30 liters per hour. The ethanol carried overhead was collected in a Dry-Ice trap. Analysis showed that 62.4 mol percent of the ethyl carbanilate had been converted and that the yield of ethanol was 88.7 mol percent and the yield of phenyl isocyanate was 87.9 mol percent both based on the ethyl carbanilate converted.

EXAMPLE II (Comparative)

In a similar run with the exception that no solvent was employed, the conversion of ethyl carbanilate was 89.2 mol percent and the yield of ethanol was 86.2 mol percent but the yield of phenyl isocyanate was only 18.1 mol percent. Infra-red and gas-liquid phase chromatographic analysis showed that the major by-product of this latter reaction is the carbodiimide which is undesirable since it is the isocyanate that is the desired useful product. This run confirmed results obtained by Dyer et al described hereinbefore.

A number of runs were carried out to produce toluene diisocyanate; all gave good selectivities. Several are shown in the following Examples.

EXAMPLE III

A mixture of 10 g diethyl toluene-2,4-dicarbamate and 50 g n-hexadecane was heated at 260° C. in a stream of nitrogen at 25 liters per hour for 1.5 hours. The reaction mixture was diluted with tetrahydrofuran and analyzed for toluene diisocyanate and the mono- and dicarbamates based on the dicarbamate charged. The yield of toluene diisocyanate was 74 mol percent and the yield of the monocarbamate was 13 mol percent, while less than 1 mol percent of the dicarbamate remained. Since the monocarbamate is an intermediate that can be recycled to produce the toluene diisocyanate this represented a potential yield of 88 mol percent of the diisocyanate.

EXAMPLE IV

A mixture of 7.2 g of diethyl toluene-2,4-dicarbamate and 36 g of ortho-terphenyl was heated at 250° C. for 2 hours in a nitrogen stream at 25 liters per hour. The product was diluted with tetrahydrofuran and the analysis showed the selectivity to toluene diisocyanate was 63.3 mol percent, the monocarbamate 27.2 mol percent and unconverted dicarbamate 3.9 mol percent. Thus the ultimate yield of the toluene diisocyanate was approximately 95 mol percent.

EXAMPLE V

A mixture of 10 g of diethyl toluene-2,4-dicarbamate was heated with 50 g of n-hexadecane at 250° C. for 4 hours in a nitrogen stream, selectivity to toluene diisocyanate was 83.4 mol percent and 9.4 mol percent to the monocarbamate. Thus the ultimate yield of toluene diisocyanate was approximately 93 mol percent.

EXAMPLE VI

A mixture of 10 g of dimethyl toluene-2,4-dicarbamate and 50 g of ortho-terphenyl was heated at 250° C. in a nitrogen stream at 50 liters per hour. The top of the reactor was heated so that substantially all of the toluene diisocyanate was carried overhead, with some of the solvent, as it was formed in the reaction. At the end of 1 hour analysis showed a 73 mol percent yield of toluene diisocyanate and a 15 mol percent yield of he monocarbamate.

EXAMPLE VII

A mixture of 10 g of diethyl toluene-2,6-dicarbamate and n-hexadecane was heated in a nitrogen stream at 30 liters per hour at a temperature of 250° C. At the end of 15 minutes the toluene-2,6-diisocyanate was 58.4 mol percent together with 34.9 mol percent of the monocarbamate and 1.8 mol percent of the starting dicarbamate. At the end of 1 hour the yield of toluene-2,6-diisocyanate was 78.1 mol percent together with 12.3 mol percent of the monocarbamate. This showed that the monocarbamate had been converted to the diisocyanate so that the ultimate yield of diisocyanate was over 90 mol percent.

EXAMPLE VIII

In this run a different ester was employed together with a mixed solvent. A mixture of 10 g of di(ethoxyethyl) toluene-2,4-dicarbamate in 20 g of tetrahydronaphthalene and 30 g of di-2-ethylhexyl phthalate was heated at 241° C. for 2 hours in a nitrogen stream at 10 liters per hour. The ethoxyethanol was carried overhead along with some of the tetrahydronaphthalene. Analysis showed an 80 mol percent conversion of isocyanate groups including a yield of 68.2 mol percent of the toluene-2,4-diisocyanate. This run showed that various esters as well as mixed solvents can be employed in the method of this invention with excellent success.

EXAMPLE IX

In order to show that runs could be carried out at low temperatures a run was carried out at 214° C. for 3 hours in which 10 g of di(ethoxyethyl) toluene-2,4-dicarbamate was heated with 50 g of tetrahydronaphthalene in a nitrogen stream at 11 liters per hour. There is obtained a 53.9 mol percent conversion to isocyanate groups including a yield of 22.3 mol percent of the toluene-2,4-diisocyanate. This run was used merely to demonstrate that the reaction could be carried out at low temperatures, however, it will be seen that the conversion is correspondingly slower.

EXAMPLE X

A mixture of 10 g of diethyl toluene-2,4-dicarbamate, 15 g of tetrahydronaphthalene and 40 g of ortho-terphenyl was heated at 259°–261° C. in a nitrogen stream at 11.4 liters per hour for 1.5 hours. The yield of toluene-2,4-diisocyanate was 66.2 mol percent along with 20.8 mol percent of the monocarbamate. This demonstrates that excellent ultimate yields of the diisocyanate can be obtained with a mixed solvent and that one solvent can be utilized as a carrier solvent.

EXAMPLE XI

A mixture of 10 g of diethyl toluene-2,4-dicarbamate and 50 g of di-2-ethylhexyl phthalate was heated in a cylindrical reactor at 250° C. for 1 hour. Nitrogen at 32 liters per hour was passed through a fritted disc at the bottom of the reactor. A yield of toluene-2,4-diisocyanate of 57.6 mol percent together with 28.6 mol percent of the monocarbamate and 2.5 mol percent of unconverted dicarbamate was obtained. This run demonstrated that ester type solvents also can be employed in the process of this invention with excellent results.

EXAMPLE XII (Comparative)

Ten grams of diethyl toluene-2,4-dicarbamate was heated in a metal bath at 250° C. for 1 hour in a nitrogen stream at 30 liters per hour. Analysis showed that only 13.3 mol percent of toluene-2,4-diisocyanate and 12.1 mol percent of the monocarbamate were obtained along with 12.4 mol percent of the dicarbamate. This shows that in the absence of solvent over 62 percent of the dicarbamate was destroyed without forming useful products while as has been shown hereinbefore the same reaction carried out in a solvent gives a dramatically higher mole percent of desired product.

EXAMPLE XIII (Comparative)

A run similar to that of Example XII except that it was carried out at 260° C. in the absence of a solvent gave a product that polymerized in the reaction flask and could not be removed from the flask. These two runs (Example XII and XIII) show the necessity of carrying out the reaction in a solvent if the high yields of the isocyanate are to be obtained.

EXAMPLE XIV

A mixture of 10 g of diisopropyl toluene-2,4-dicarbamate and 50 g of n-hexadecane was heated at 250° C. in a nitrogen stream at 25 liters per hour bubbling through the solution. Conversion to toluene-2,4-diisocyanate was 45 mol percent at the end of 1-½ hours. This run shows that secondary alcohol esters of the dicarbamic acid are amenable to the process of this invention.

EXAMPLE XV

A mixture of 10.7 g (0.03 moles) 1,6-hexylene dicarbanilate

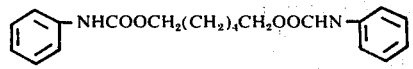

and 50 g n-hexadecane was heated at 250° C. for two hours in a nitrogen stream at 50 liters per hour. Analysis of the products taken overhead during the run showed that the yield of phenyl isocyanate produced under these conditions was 57.2 mol percent. The material remaining in the pot was unreacted carbamates so longer reaction time would have produced additional phenyl isocyanate at a very high ultimate yield.

EXAMPLE XVI

A mixture of 10 grams of diethyl toluene-2,4-dicarbamate and 50 grams of technical grade n-octadecane was heated at 250° C. in a stream of nitrogen at 30 liters per hour for 1 hour. The yield of toluene diisocyanate was 59.8 mole percent and the yield of the monocarbamate was 24.4 mole percent while 1.4 mole percent of the dicarbamate remained unreacted. Thus the ultimate yield of toluene diisocyanate was approximately 86 mole percent.

As pointed out hereinbefore, alkyl substituted benzenes having from 1 to 15 carbon atoms in the alkyl side chain can be employed as the solvent. The monoalkyl benzenes having from 9 to 15 carbon atoms in the alkyl side chain are particularly useful and are available as so-called "detergent alkylate" since these compounds when sulfonated and neutralized produce the alkyl benzene sulfonates widely used in both household and industrial detergent formulations. The detergent alkylates are available generally as mixtures of compounds varying only in the number of carbon atoms in the side chain. For example, the commercial material may contain from 10 to 15 carbon atoms in the side chain with over 90 weight per cent of the compounds having from 12 to 14 carbon atoms in the side chain and with the average being 13 carbon atoms in the side chain. Other commercial materials have other distributions of alkyl side chains. The alkyl side chains may be either straight chain or branched chain, but most commercial detergent alkylate available in recent years contains only straight chain compounds since these give biodegradable detergents whereas the branched chain compounds give detergents resistant to biodegradation and hence are no longer in general use.

The following examples are provided to show the use of commercial detergent alklates as solvents.

EXAMPLE XVII

A mixture of 10 g diethyl toluene-2,4-dicarbamate and 50 g of a commercial detergent alkylate, having about 10 to 12 carbon atoms in the alkyl side chain, with small amounts of higher and lower compounds and with an average side chain of about 11.3 carbon atoms attached to the benzene ring, was heated at 250° C. in a stream of nitrogen at 30 liters per hour for 1 hour. The reaction mixture was diluted with tetrahydrofuran and analyzed for toluene diisocyanate and the mono- and dicarbamates based on the dicarbamate charged. The yield of toluene diisocyanate was 52 mole per cent and the yield of the monocarbamate was 41.6 mole per cent, while 4 mole per cent of the dicarbamate remained. Thus, the ultimate yield of the toluene diisocyanate was over 97 mole per cent.

EXAMPLE XVIII

A mixture of 10 g diethyl toluene-2,4-dicarbamate and 50 g of a commercial detergent alkylate having from 10 to 15 carbon atoms in the side chain, with over 90 weight per cent having from 12 to 14 carbon atoms and with an average side chain of 13 carbon atoms attached to the benzene ring, was heated at 250° in a stream of nitrogen at 30 liters per hour for 1 hour. The yield of toluene diisocyanate was 59.1 mole per cent and the yield of monocarbamate was 25.7 mole per cent while 1.4 mole per cent of the dicarbamate remained. Thus, the ultimate yield of toluene diisocyanate was over 86 mole per cent.

In order to demonstrate continuous operation, the following runs were made.

EXAMPLE XIX

The detergent alkylate of Example XVII in the amount of 100 ml was placed in a 300 ml round-bottom flask fitted with two feed inlet tubes, a nitrogen inlet tube, a 12 inch Vigreaux column, a thermometer and a product dip tube. A solution containing 0.12 g diethyl toluene-2,4-dicarbamate per ml of tetrahydrofuran solution was pumped in at the rate of about 32 ml per hour; the detergent alkylate was pumped in at approximately 8 to 10 ml per hour to maintain a level sufficient to give an average residence time of about 15 hours. A stream of nitrogen was passed in at a rate of 30 liters per hour. The pot temperature was maintained at 250° C and the column was wrapped to give a temperature of 130° C at the top of the column. Under steady state conditions, the yield of toluene diisocyanate recovered overhead was 81 mole per cent along with 3 mole per cent of monocarbamate. In addition, 2 mole per cent toluene diisocyanate, 5 mole per cent monocarbamate and 2 mole per cent dicarbamate were present in the product drawn from the pot to give a total yield of 93 mole per cent.

EXAMPLE XX

In the same unit as described in Example XIX, the detergent alkylate was replaced with n-hexadecane. Other conditions were similar except for a top column temperature of 180°C. Under steady state conditions with an average residence time of about 20 hours, the yield of toluene diisocyanate recovered overhead was 84 mole per cent along with 9 mole per cent monocarbamate. In addition, 1 mole per cent toluene diisocyanate, 2 mole per cent monocarbamate and 1 mole per cent dicarbamate were present in the product drawn from the pot to give a total yield of 97 mole per cent.

Examples XVII and XVIII show that alkyl benzenes having up to 15 carbon atoms in the alkyl side chain, i.e. the detergent alkylates can be employed as solvents in the method of this invention. Examples XIX and XX demonstrate continuous operation and show that exceedingly high yields are obtainable thereby.

All the foregoing examples demonstrate the utility of the invention for generating isocyanates corresponding to various esters of various carbamic acids by utilizing the solvent method of this invention with atmospheric pressure pyrolysis. The results show that high yields of isocyanates are obtainable even from esters of dicarbamic acids which heretofore, in general, gave little if any yield of the diisocyanate by pyrolysis methods. Of particular interest the results show that in the conversion of the dicarbamates there is formed the monocarbamate intermediate which on continued conversion (or recycle) is converted to the diisocyanate.

We claim:

1. A method for the production of isocyanates from esters or carbamic acids having the formula $R(NHCOOR')_x$ or $(RNHCOO)_xR'$ wherein R is a substituted or unsubstituted mono-, di- or trivalent organic radical selected from the group consisting of a saturated or monoolefinic unsaturated straight or branched chain aliphatic or cycloaliphatic radical containing not more than 32 carbon atoms, an alkoxyalkyl radical having not more than 32 carbon atoms, an aryl radical, an aralkyl radical, and an alkaryl radical containing 1 to 5 rings; R' is a substituted or unsubstituted mono-, di- or trivalent radical selected from the group consisting of a saturated or monoolefinic unsaturated straight or branched chain aliphatic or cycloaliphatic radical containing not more than 32 carbon atoms, an alkoxyalkyl having not more than 32 carbon atoms, an aryl radical, an aralkyl radical, and an alkaryl radical containing 1 to 3 rings; and x is 1, 2 or 3, and R and R' being the same or different, respectively, where x is 2 or 3, which comprises thermally decomposing said ester at a temperature in the range of from 175°C. to 350°C. while said ester is dissolved in an inert solvent to produce the isocyanate and alcohol, said solvent being characterized as a compound which is (a) a solvent for said ester, (b) liquid and stable at said reaction temperature and (c) non-reactive with said isocyanate produced in said thermal decomposition reaction and selected from the group consisting of aliphatic hydrocarbons having from 4 to 32 carbon atoms, the halo- and mono-nitro substituted derivatives of said aliphatic hydrocarbons, cycloaliphatic hydrocarbons, or aromatic hydrocarbons having from 1 to 3 rings, the alkyl benzenes having from 1 to 15 carbon atoms in the alkyl group, the halo- and mono-nitro substituted derivatives of said aromatic hydrocarbons, oxygenated compounds containing from 4 to 32 carbon atoms selected from the group consisting of ethers, ketones, and esters of organic carboxylic acids and sulfur analogues of said oxygenated compounds, and separately recovering said isocyanate and alcohol.

2. The method according to claim 1 wherein said solvent is ortho-terphenyl.

3. The method according to claim 1 wherein said solvent is tetrahydronaphthalene.

4. The method according to claim 1 wherein said solvent is a mixture of alkyl benzenes having from 9 to 15 carbon atoms in the alkyl group.

5. The method according to claim 1 wherein said mixture of alkyl benzenes has from 10 to 12 carbon atoms in the alkyl group with an average of about 11 carbon atoms.

6. The method according to claim 1 wherein said mixture of alkyl benzenes has from 10 to 15 carbon atoms in the alkyl group with an average of about 13 carbon atoms.

7. The method according to claim 1 wherein said solvent is n-hexadecane.

8. The method according to claim 1 wherein said solvent is n-octadecane.

9. The method according to claim 1 wherein said oxygenated compound is di-2-ethylhexyl phthalate.

10. The method according to claim 1 wherein R is selected from the group consisting of mono-, di- and trivalent unsubstituted organic aliphatic radicals containing up to 18 carbon atoms, halo- or mono-nitro substituted mono-, di- or trivalent organic aliphatic radicals containing up to 18 carbon atoms, mono-, di- and trivalent cycloaliphatic radicals containing from 5 to 7 carbon atoms, mono-unsaturated cycloaliphatic radicals having from 5 to 7 carbon atoms, substituted cycloaliphatic radicals wherein the substituent is a lower alkyl radical having 1 to 4 carbon atoms, a nitro radical or a chloro radical, alkoxyalkyl radicals having up to 18 carbon atoms, and mono-, di- or trivalent unsubstituted aryl radicals having from 1 to 5 rings, aryl radicals substituted with 1 or more alkyl groups having from 1 to 4 nitro groups or halo groups, and aralkyl radicals wherein the alkyl portion contains from 1 to 4 carbon atoms and the aryl contains from 1 to 3 rings; R' is selected from the group consisting of mono-, di- and trivalent unsubstituted organic aliphatic radicals containing up to 18 carbon atoms, halo or mono-nitro substituted mono-, di- or trivalent organic aliphatic radicals containing up to 18 carbon atoms and alkoxyalkyl radicals containing up to 18 carbon atoms.

11. The method according to claim 1 wherein the decomposition temperature is in the range of from 200°C. to 300°C. and the solvent is selected from the group consisting of ortho-terphenyl, tetrahydronaphthalene, alkyl benzenes having from 9 to 15 carbon atoms in the alkyl group, n-hexadecane, n-octadecane, and di-2-ethylhexylphthalate.

12. The method according to claim 11 wherein said mixture of alkyl benzenes has from 10 to 12 carbon atoms in the alkyl group with an average of about 11 carbon atoms.

13. The method according to claim 11 wherein said mixture of alkyl benzenes has from 10 to 15 carbon atoms in the alkyl group with an average of about 13 carbon atoms.

14. A method for the production of a toluene diisocyanate from an ester of carbamic acid said ester being selected from the group consisting of dimethyl toluene-2,4-dicarbamate, diethyl toluene-2,4-dicarbamate, dipropyl toluene-2,4-dicarbamate, diisopropyl toluene-2,4-dicarbamate, dibutyl toluene-2,4-dicarbamate, diamyl toluene-2,4-dicarbamate, dihexyl toluene-2,4-dicarbamate, diphenyl toluene-2,4-dicarbamate, di(phenylmethyl)toluene2,4-dicarbamate, dinaphthyl toluene-2,4-dicarbamate, di(ethoxyethyl)toluene-2,4-dicarbamate and the corresponding esters of toluene-2,6-dicarbamate, which comprises thermally decomposing said ester at a temperature in the range of from 175°C. to 350°C. while said ester is dissolved in an inert solvent to produce the toluene diisocyanate and the corresponding alcohol, said solvent being characterized as a compound which is (a) a solvent for said ester, (b) liquid and stable at said reaction temperature and (c) non-reactive with said isocyanate produced in said thermal decomposition reaction and selected from the group consisting of aliphatic hydrocarbons having from 4 to 32 carbon atoms, the halo- and mono-nitro substituted derivatives of said aliphatic hydrocarbons and, cycloaliphatic or aromatic hydrocarbons having from 1 to 3 rings, alkyl benzenes having from 1 to 15 carbon atoms in the alkyl group, the halo- and mono-nitro substituted derivatives of said aromatic hydrocarbons, oxygenated compounds containing from 4 to 32 carbon atoms selected from the group consisting of ethers, ketones, and esters of organic carboxylic acids and sulfur analogues of said oxygenated compounds, and separately recovering said toluene diisocyanate and the corresponding alcohol.

15. The method according to claim 14 wherein said toluene diisocyanate is toluene-2,4-diisocyanate.

16. The method according to claim 14 wherein said toluene diisocyanate is toluene-2,6-diisocyanate.

* * * * *